United States Patent [19]

Mathis et al.

[11] 4,404,311

[45] Sep. 13, 1983

[54] NOVEL COMPOUNDS AND THEIR USE IN ELASTOMER-CONTAINING COMPOSITIONS

[75] Inventors: Thomas C. Mathis, St. Louis, Mo.; Albert W. Morgan, Collinsville, Ill.

[73] Assignee: Monsanto Company, St. Louis, Mo.

[21] Appl. No.: 422,620

[22] Filed: Sep. 24, 1982

Related U.S. Application Data

[60] Division of Ser. No. 290,621, Aug. 10, 1981, Pat. No. 4,368,341, which is a continuation-in-part of Ser. No. 187,232, Sep. 15, 1980, abandoned.

[51] Int. Cl.$^3$ ............................ C08K 5/01; C08K 5/03
[52] U.S. Cl. ...................................... 524/486; 260/759
[58] Field of Search ................. 524/486, 484; 260/759

[56] References Cited

U.S. PATENT DOCUMENTS

| | | | |
|---|---|---|---|
| 2,172,391 | 9/1939 | Krase | 260/649 |
| 2,364,719 | 12/1944 | Jenkins | 260/666 |
| 2,790,014 | 4/1957 | Marshall | 260/666.5 |
| 2,925,398 | 2/1960 | Coran et al. | 260/33.6 |
| 3,058,930 | 10/1962 | Samour | 260/4 |
| 3,322,841 | 5/1967 | Geering | 260/668 |
| 3,331,782 | 7/1967 | Deltieure | 252/186 |
| 3,418,259 | 12/1968 | Kennedy et al. | 260/2 |
| 3,579,582 | 5/1971 | Lombard | 260/574 |
| 3,676,166 | 7/1972 | Louthan | 106/241 |
| 3,827,999 | 8/1974 | Crossland | 260/33.6 AQ |
| 3,829,526 | 8/1974 | Doss et al. | 260/75 |
| 3,935,134 | 1/1976 | Dollhausen et al. | 260/3.5 |

OTHER PUBLICATIONS

Synthesis and Properties of Some Linear Oligobenzyls and Polybenzyls, G. Montaudo et al., 8 *J. Polym. Sci.,* (A-1) 2453-2464 (1970).
Polycondensation of Benzyl Chloride and its Derivatives: A Study of the Reaction at Different Temperatures, G. Montaudo et al., 8 *J. Polym. Sci.* (A-1) 2475-2490 (1970).
Poly(arylenealkyls), I. I. Yukel'son et al., 38(12) *Russian ChemicalReviews,* 966 (1969).
Factors in Tackification, C. DeWalt, *Adhesives Age,* Mar. 1970.
Tack and Viscoelasticity of Block Copolymer Based Adhesives, G. Kraus et al., 10 *J. Adhesion,* 221-236 (1979).
Path of Partial Hydrogenation of o-, m-, and p-Terphenyl, D. A. Scola et al., vol. 30, No. 3, *J. Org. Chem.,* 384-388 (Feb. 1965).
HB-40 ® Hydrogenated Terphenyl, Monsanto Company, St. Louis, Mo. (Sep. 1973).
Surface Treating Agent for Adhering a Vulcanized Rubber, Inahara, *Chem. Abstracts* 126391q, vol. 82(20) (1975).

*Primary Examiner*—Joseph I. Schofer
*Assistant Examiner*—J. M. Reddick
*Attorney, Agent, or Firm*—George R. Beck; A. Milton Cornwell; Arnold H. Cole

[57] ABSTRACT

Elastomeric polymers are rendered more tractable, thereby decreasing the amount of vehicle or heat required for vehicle- or melt-deposition, while resulting in very little or no loss of strength of the polymer, by the use of at least one compound comprising at least three hydrocarbon rings including at least one aromatic ring and, in most embodiments, at least one saturated ring free to rotate independently of at least one aromatic ring in the molecule of that compound. Compositions comprising an elastomeric polymer and at least one such compound are especially attractive for use in solvent, latex and/or hot melt adhesive compositions.

21 Claims, No Drawings

NOVEL COMPOUNDS AND THEIR USE IN ELASTOMER-CONTAINING COMPOSITIONS

This is a division, of application Ser. No. 290,621, filed Aug. 10, 1981, which is a continuation-in-part of application Ser. No. 187,232, filed Sept. 15, 1980, now abandoned.

BACKGROUND OF THE INVENTION

Elastomeric polymers have a great variety of uses, e.g., in adhesives, electrical insulation, inks, sealants, paints, lacquers, varnishes and other coatings. In general, these polymers (hereinafter at times called "elastomers") have such versatility because they are two-phase or multi-phase substances in which one phase (typically called the "rubber" phase) contributes elasticity and another phase (normally more crystalline) provides tensile strength and dimensional stability. In many uses, these polymers are dissolved, emulsified or otherwise dispersed in a suitable liquid vehicle which facilitates their handling (e.g., for deposition on a solid surface) after which most or essentially all of the vehicle is removed, typically by evaporation, leaving the elastomer in position for the desired end use. This technique is widely practiced, but has significant disadvantages.

More specifically, most of such elastomers require the use of volatile organic (particularly aromatic vehicles to adequately dissolve their more crystalline phases at room temperature and concentrations of at least about 50% (in some cases at least about 30%). However, such vehicles can pose environmental pollution problems, worker inhalation dangers and/or explosion hazards. In addition, there are various costs that increase with the amount of vehicle employed, e.g. shipping expense, losses to the atmosphere, and equipment and procedures for vehicle recovery (in some cases with recycle).

In other, equally important elastomer applications the need for a vehicle is diminished or avoided by applying the elastomer in molten form, but this requires additional energy to melt the elastomer and can result in partial degradation of the polymer. The higher the temperature needed to melt the elastomer, the greater the energy requirement and degradation potential.

Usually, the problems of elastomer deposition can be at least partly overcome by the use of a relatively nonvolatile substance that renders the elastomer more tractable, i.e., a plasticizer, but this generally has the drawback of lessening the cohesion of the elastomer and thereby decreasing its strength in the intended end use. Thus the substances which tend to decrease the amount of organic vehicle and/or energy needed for deposition of the elastomer typically diminish the strength of the elastomer after evaporation of the solvent and/or resolidification of the elastomer. Minimizing this loss of strength is critically important for most uses of the elastomers, e.g. in adhesives, protective coatings, etc.

An object of this invention is a class of compounds having attractive utilities, particularly in providing attractive elastomer compositions. Another object is elastomer compositions containing such compounds, including elastomer compositions useful in satisfactory deposition or other handling of the elastomer, especially with little or no adverse effect on elastomer strength. Another object is elastomer compositions which can be solvent-, latex- or melt-deposited without requiring excessive energy for vehicle removal or melting of the elastomer. Other objects are to decrease pollution problems, explosion hazards and/or other personnel dangers from vehicle removal, the costs of transporting vehicle-containing elastomer compositions and/or ultimately the unit cost of articles containing the elastomer. Other objects include elastomer compositions having good adhesive properties, and a class of novel compounds useful in providing such compositions. These and other objects will be more readily understood from the following disclosure in which all parts and percentages are by weight and all temperatures are in degrees Celsius except as otherwise noted.

SUMMARY OF THE INVENTION

It has now been discovered that the foregoing objects can be substantially achieved by the use of certain compounds comprising at least three hydrocarbon rings, at least one of which is aromatic. Thus in one embodiment the invention provides a class of novel compounds consisting of at least 5 hydrocarbon rings including at least one aromatic ring and at least one saturated ring free to rotate independently of at least one aromatic ring in the molecule of said compound, at least one divalent aliphatic radical linking to of said rings, and from zero to about two alkyl substituents on said rings, said compounds having molecular weights between about 400 and about 8000. Also provided by the invention is a wide variety of useful compositions comprising a normally solid, essentially organic elastomer and at least one compound from the class just described.

In another embodiment the invention is directed to compositions containing such as elastomer and at least one compound consisting of at least 3 hydrocarbon rings including at least one aromatic ring and at least one saturated ring free to rotate independently of at least one aromatic ring in the molecule of said compound, said compound having a molecular weight between about 200 and about 2000.

In another embodiment the invention is directed to compositions containing such an elastomer and at least one compound consisting of at least 5 aromatic hydrocarbon rings, a plurality of divalent aliphatic radicals each linking two of said rings, and from zero to about two alkyl substituents on said rings, said compound having a molecular weight between about 400 and about 4000, and said plurality being at least half the number of rings in said compound.

In accordance with this invention it has been found that combining at least one such compound with the elastomer substantially facilitates vehicle- or melt-deposition of the elastomer, while in most cases unexpectedly resulting in very little or essentially no loss in strength of the deposited elastomer. Accordingly, in many instances such elastomer-containing compositions have surprisingly great strength when used in adhesives, surface coatings, etc.

DETAILED DESCRIPTION OF THE INVENTION

As used herein, the term "elastomer" refers to normally solid, relatively high molecular weight (MW) polymers that stretch under tension, have a relatively high tensile strength, retract rapidly and essentially recover their original dimensions. Within the context of this invention, these polymers are essentially organic, i.e., their molecular structures are devoid of inorganic elements having a substantial effect on the properties of such polymers. Typical examples include natural rubber (essentially poly(cis-1,4-isoprene)), synthetic rubbers such as homopolymers of acyclic hydrocarbon or halohydrocarbon dienes such as, e.g. butadiene, chlorobutadiene or isoprene, copolymers of such monomers, e.g. butadiene-styrene, isoprene-styrene, acrylonitrile-styrene, acrylonitrile-butadiene-styrene, butadiene-acrylonitrile (nitrile rubber) and isobutylene with small amounts of isoprene (butyl rubber), polyacrylates, various polyamides and polysulfide, silicone, ethylene-propylene (optionally diene-modified) and urethane rubbers. Other important examples include polyvinyl acetate and copolymers of vinyl acetate (e.g. with $C_2-C_4$ olefins such as ethylene) in which the proportion of vinyl acetate monomer is at least about 10% (usually at least about 15% and even more typically at least about 20%) up to about 50% (generally less than 35% and preferably from about 25% to about 30% for many hot-melt adhesive uses).

Of particular utility in this invention are elastomers in which the polymer chain(s) consist essentially of carbon atoms. Even more preferred in some embodiments (especially for solvent- or latex-deposition) are the hydrocarbon elastomers (those containing only carbon and hydrogen) such as, e.g. natural rubber, polymers of at least one diene containing from 4 to about 5 carbon atoms, e.g. butadiene or isoprene, copolymers of styrene and at least one such diene, and mixtures thereof. These copolymers include, e.g. the widely-used triblock copolymers of styrene and butadiene (SBS) or isoprene (SIS) and multiblock copolymers of styrene with either of such dienes, as well as "random" copolymers of styrene and butadiene (SBR) which normally contain polystyrene blocks. These copolymers are two-phase or multi-phase substances in which relatively amorphous (typically aliphatic) domains which are normally substantially soluble in aliphatic solvents (e.g. n-hexane) provide flexibility, and relatively crystalline (usually aromatic) domains which are normally substantially soluble in aromatic solvents (e.g. toluene) but not substantially soluble in such aliphatic solvents provide strength and dimensional stability. These several phases thus have various different properties such as, e.g. glass transition temperatures, melting ranges, etc. Most commonly the more crystalline domains constitute at least about 15% (e.g. at least 14%) of such elastomers. Many of such elastomers and their properties are described in THE VANDERBILT RUBBER HANDBOOK, edited by George G. Winspear, R. T. Vanderbilt Company, Inc., New York, N.Y. (1968), pertinent portions of which are incorporated herein by reference.

As aforesaid, the elastomer compositions to which this invention relates are typically useful in depositing the elastomer on a solid surface, e.g. for use as an adhesive, a sealant or a protective, insulating or decorative coating. By way of illustration, embodiments of this invention have utility in polyacrylate paint and lacquer compositions, polysulfide sealant compositions and, especially advantageously, adhesive compositions useful in solvent-based, water emulsion (latex) and/or hot-melt adhesives. Common adhesive formulations and elastomers useful therein are further described in ADHESION AND THE FORMULATION OF ADHESIVES by W. C. Wake, Applied Science Publishers, Ltd., London (1976), "Factors in Tackification", C. DeWalt, ADHESIVES AGE (March 1970) and "Tack and Viscoelasticity of Block Copolymer Based Adhesives", G. Kraus et al, 10 J. ADHESION 221-36 (1979), the disclosures of which are incorporated herein by reference.

As aforesaid, the elastomer modifying compounds which provide the advantages described herein contain at least three hydrocarbon rings, at least one of which is aromatic. Normally, some of these compounds are liquid, others are semi-solid and others are solid. In general they have relatively low volatility, especially in relation to commonly used hydrocarbon solvents such as toluene, xylene, benzene, hexanes, heptanes, etc.

In many important embodiments, each of such compounds contains at least one saturated ring free to rotate independently of at least one aromatic ring in the molecule of that compound. As used herein, "free to rotate independently" means the two rings are not fused or otherwise linked together such that one ring cannot rotate independently of the other. Thus, in the absence of additional linkages preventing independent rotation, two rings linked directly (solely) through a carbon-to-carbon single bond (as in, e.g., biphenyl or cyclohexyl benzene) or a divalent aliphatic radical (as in, e.g., diphenylmethane or benzyl cyclohexane) are free to rotate independently.

Compounds Containing At Least One Aliphatic Linkage

In an especially attractive class of compounds of this invention, each compound contains at least one divalent aliphatic radical through which two of the hydrocarbon rings in that compound are directly linked. Preferred embodiments of those compounds contain at least two, and usually even more desirably at least three such direct ring-to-ring aliphatic linkages, preferably in the longest chain of carbon atoms in that compound. Even more preferred for some uses are such compounds in which each of a majority of the rings therein is directly linked to at least one other ring through such an aliphatic radical, and especially those in which each of at least one (more desirably at least two, three or even more) saturated ring(s) is/are directly linked to at least one aromatic ring through such an aliphatic radical. Compounds useful in another embodiment of the invention contain a plurality of divalent aliphatic radicals each linking two of the rings in that compound, said plurality being at least about half (preferably at least about 70% and generally even more desirably at least about 85%) of the number of rings in that compound, and some elastomer compositions containing at least one such compound have good adhesive properties even when the compound is essentially or completely devoid of saturated rings.

Normally for best results, such aliphatic (i.e., acyclic) radicals are lower ($C_1-C_4$) alkylene, especially $-(CH_2)_m-$ wherein m is one or two, and most desirably methylene, e.g. as in a compound resulting from benzylation of an unsaturated cyclic starting material, e.g. toluene, a polyphenyl or cyclohexene, before, after or without partial hydrogenation as described herein. Thus for most uses, the hydrocarbon rings in these compounds constitute generally at least about 75%, and preferably at least about 80% of the molecular weight of such compounds.

These compounds may also contain non-linking ring substituents, e.g. alkyl groups, which do not preclude satisfactory use of those compounds as disclosed herein. Preferably the number of such substituents in the compound is from zero to about two, although otherwise-similar compounds having additional ring substituents may provide satisfactory results in some cases. These ring substituents are preferably lower alkyl, especially methyl or ethyl (most desirably methyl) although non-alkyl substituents (even non-hydrocarbon substituents such as halogens, etc.) may be tolerable in some uses.

The number of hydrocarbon rings in these compounds is preferably from 5 to about 25 although some variations with fewer than about 5 or more than about 25 may be useful. These compounds contain even more preferably at least 6 rings (usually most advantageously at least 7 rings) and also more preferably up to about 15 rings (generally more desirably up to about 12 rings and most advantageously up to 11 rings). As can be seen from specific examples herein, best results are obtained in some instances with compounds containing from 5 to about 8 rings, while in other instances superior results are achieved with compounds containing from about 9 to about 12 rings. Most commonly the MW's of these compounds are at least about 400, preferably at least about 475, and typically most advantageously at least about 550. Also most commonly such MW's may be as high as about 8000 or higher (preferably not above about 6000 and for some uses most desirably not above about 4000).

Exemplary of these compounds are those prepared at least in part by benzylating (usually most conveniently by a reaction of the Friedel-Crafts variety) an unsaturated hydrocarbon starting material, e.g. toluene, xylene, ethyl benzene, benzyl chloride, biphenyl, a terphenyl, a quarterphenyl, diphenylemthane, styrene, α-methyl styrene, cyclohexene, cyclohexadiene, or the like. Illustrations of such polybenzylation reactions may be found in U.S. Pat. No. 3,322,841 issued May 30, 1967 to E. J. Geering; U.S. Pat. No. 3,418,259 issued Dec. 24, 1968 to J. P. Kennedy et al.; "Synthesis and Properties of Some Linear Oligobenzyls and Polybenzyls" by G. Montaudo et al, 8 J. POLYM. SCI. (A-1) 2453 and 2475 (1970); and "Poly(alkylenealkyls)" by I. I. Yukel'son et al., 38(12) RUSSIAN CHEMICAL REVIEWS 966 (1969), the disclosures of which are incorporated herein by reference. In such benzylation reactions, the benzyl radicals may become situated individually on reactive sites on the unsaturated starting material and/or they may add to one another polymerically forming oligomeric polybenzyl substituents on the starting material, depending on reaction conditions, the proportions of reactants, the nature of the starting material, etc.

In some embodiments these relatively highly aromatic benzylation products are subjected to partial hydrogenation, which can be carried out by any suitable procedure, e.g. in the presence of molecular hydrogen and a hydrogenation catalyst (such as Raney nickel or cobalt, platinum, palladium or the like) at a temperature of 180°–240° and a pressure of 500–1000 psig. Desired degrees of such hydrogenation are discussed hereinafter.

Other examples of these compounds can be prepared by cycloalkylating (e.g. cyclohexylating) an unsaturated compound containing at least one aliphatic linkage, e.g. a diphenylalkane or a compound obtained by benzylating an unsaturated hydrocarbon starting material. The cycloalkylation can be carried out by any convenient alkylation procedure, e.g. reacting that starting material with a cycloolefin at an elevated temperature (usually up to about 100°) in the presence of a suitable catalyst such as $AlCl_3$ and optionally anhydrous HCl. These compounds may be partially hydrogenated before or after such cycloalkylation and, in fact, it is normally preferred to establish the desired number of saturated rings in the compounds used in this invention at least partially by hydrogenation. Those prepared at least partially by hydrogenation typically exhibit somewhat more attractive properties in the elastomer compositions of this invention, possibly because of a relatively random (rather than solely terminal) distribution of saturated rings within such compounds.

COMPOUNDS CONTAINING NO ALIPHATIC LINKAGES

In the aforementioned class of compounds consisting of at least 3 hydrocarbon rings including at least one aromatic ring and at least one saturated ring free to rotate independently of at least one aromatic ring in that compound, each of the linkages between the rings is a carbon-to-carbon single bond. For use in solvent deposition of many elastomers, these compounds contain preferably from 3 to about 5 rings, while for use in hot-melt elastomer deposition it is usually advantageous that they contain from 5 to about 12 rings (usually most desirably up to about 10 rings). Most commonly the MW's of these compounds are at least about 200 (preferably at least about 225) and may be as high as about 2000 or more (preferably not above about 1500 for some uses).

These compounds are exemplified by those having the structural formula

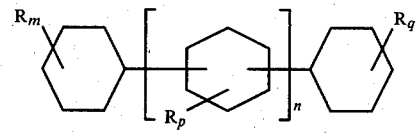

wherein each R is independently phenyl or cycloalkyl, n is zero or an integer from one to about three, m and q are each independently zero or an integer from one to five, p is zero or an integer from one to four, and the sum of m, n, p and q is from one to about thirteen.

Compounds of this kind containing three or four rings can be prepared by partial hydrogenation of by-products (o-terphenyl, m-terphenyl, p-terphenyl and the various isomeric quaterphenyls) formed during synthesis of biphenyl by pyrolysis of benzene. These compounds have been described as useful as light stabilizers for monoolefinic polymers, plasticizers for various resins including polysulfides and chlorinated rubber, swelling agents for rubber compounds and enhancers of the miscibility of synthetic rubber latex with mineral oil. See U.S. Pat. Nos. 2,364,719 issued Dec. 12, 1944 to R. L. Jenkins, 2,925,398 issued Feb. 16, 1960 to A. Y. Coran et al., 3,331,782 issued July 18, 1967 to R. P. Deltieure, and commercial literature on HB-40 ® partially hydrogenated terphenyl published in September 1973 by Monsanto Company, St. Louis, Mo. Preparations of such hydrogenated polyphenyls are described in U.S. Pat. Nos. 2,790,014 issued Apr. 23, 1957 to W. W. Marshall, 3,829,526 issued Aug. 13, 1974 to R. C. Doss et al., and "Path of Partial Hydrogenation of o-, m-, and p-Terphenyl", D. A. Scola et al., Vol. 30, No. 3, J. ORG. CHEM. 384-88 (February 1965), the disclosures of which are incorporated herein by reference.

Other compounds within this class can be prepared by cycloalkylation of biphenyl, the various terphenyls or quaterphenyls, higher polyphenyls and/or products of partial or complete hydrogenation thereof, by any convenient alkylation procedure, e.g. as described in U.S. Pat. No. 3,935,134 issued Jan. 27, 1976 to M. Dollhausen et al, which discloses that various alkylated polyphenyls are useful in heat-sealing adhesives containing, in combination, a modified olefin polymer, a chlorinated olefin or diene polymer, an aromatic polynitroso compound and an organic solvent. The disclosure of that patent is incorporated herein by reference.

Typically all of the rings in the hereindescribed multiring compounds exist as monocyclic ring structures containing from about 5 to about 12 (preferably 6) carbon atoms per ring, e.g. phenyl(ene) or cyclohexyl(ene), but in some instances at least a portion of them can be present in fused ring structures, e.g. naphthyl(ene) or decahydronaphthyl(ene). Although the rings of principal interest are hydrocarbon (consisting of carbon and hydrogen), it is believed that some heterogeneous rings, e.g. thiophenyl or pyridyl, may provide similar results and in such cases should be considered equivalents of the aforementioned hydrocarbon rings. Similarly, equivalent results may be obtained in some cases when at least a portion of the aforementioned divalent aliphatic ring linking radicals are replaced with other noncyclic linking radicals, e.g. ester, amide or vinyl radicals, —O—, —S—, etc.

Mixtures of any of the aforementioned multi-ring compounds can also be used, in some instances with advantageous results. In many of such embodiments of the invention there are employed compositions comprising a mixture of non-isomeric compounds in which the ratio of average MW by wt. to average MW by number is greater than 1.0 and may be as high as about 3 or even higher. In general, using mixtures of the compounds having at least one aliphatic linkage, best results are obtained when such mixtures have average MW's (by wt.) of at least about 400 (preferably at least about 450) up to about 2500 (in some cases preferably up to about 2000). Using mixtures of the compounds having no aliphatic linkages, best results are usually obtained when the average MW of the mixture (by wt.) is at least about 200 (preferably at least about 225) up to about 1500 (preferably up to about 1250 in some instances). In general, the variation of compound MW's within such a mixture has a beneficial effect on strength of the elastomer in adhesives, surface coatings, etc.

Usually, although not always, good results are obtained when, on the average, from about 20% to about 80% of the hydrogen atoms in the compounds employed are situated in the aromatic ring(s) in those compounds, with the rest of such hydrogen atoms situated in such saturated rings, aliphatic ring-linking radicals and/or alkyl ring substituents as are present in those compounds. Superior results are usually attained when the aromatic rings contain from about 25% to about 70% of the hydrogen atoms in such compounds. In certain embodiments, e.g. those utilizing an elastomer selected from the aforementioned ethylene/vinyl acetate copolymers, best results are often achieved when the aromatic rings contain from about 30% to about 60% of the hydrogen atoms in such compounds. However, the optimum level of hydrogenation may vary with the nature of the surface to which the elastomer composition is to be applied. Thus, as shown in specific examples hereinafter, the best adhesion to some surfaces is obtained when from about 25% to about 45% of the hydrogen atoms are situated in aromatic rings (especially in compounds containing from 5 to about 8 rings) while for adhesion to other surfaces it is preferable that from about 45% to about 70% of the hydrogen atoms are in aromatic rings. Hereinafter, this percentage of hydrogen atoms situated in aromatic rings of a given compound is generally referred to as the "aromatic hydrogen percentage" or "AHP" of that compound. Normally, this percentage is conveniently determined by proton NMR.

Referring to use of the aforementioned compounds consisting of hydrocarbon rings without aliphatic linkages in solvent-based elastomer compositions, good results are generally obtained when from about 20% to about 80% of the rings in such compounds are aromatic, with the rest being saturated; superior results are usually attained when the percentage of aromatic rings is from about 50% to about 70% are, in certain embodiments using elastomeric copolymers of styrene and at least one $C_4$–$C_5$ diene, from about 55% to about 65%, the rest being saturated. In such cases, especially good results (e.g. in adhesive tack stability) are achieved when those compounds are predominantly, or even more desirably at least about 75%, quaterphenyls.

Any of the aforedescribed compounds can be used in the elastomer compositions of this invention in any amount and concentration sufficient to substantially achieve one or more of the objects of this invention. Surprisingly, these compounds have been found to raise the lowest glass transition temperature ($T_g$) of many of such elastomers, i.e., that of the rubber phase of such elastomers, and in preferred embodiments of the invention such compounds are used in an amount and concentration sufficient to raise that $T_g$, such amount and concentration normally increasing or at least not decreasing the strength of the elastomer at typical end use temperatures such as, e.g., 25° C.

In general, objects of this invention are realized when such compounds are present in an amount substantially greater than 15%, more commonly at least about 20%, preferably at least about 25% and usually even more desirably at least about 30%, based on the elastomer in that composition. Normally those compounds will be present in such a composition in an amount up to about 100% or more by wt. of the elastomer, although in many embodiments up to about 55% by wt. of the elastomer will be sufficient. Based on other normally solid constituents of such compositions (elastomers and common additional constituents such as, e.g., waxes, tackifiers, nonelastomeric resins, fillers, pigments, dyes, lubricants, antioxidants, etc.) such compounds are typically present in the amount of at least about 10%, more usually at least about 15% and most commonly at least about 20% of such solids. Normally such compounds are present in an amount up to about 50% or more (most commonly up to about 30%) of such solids.

As mentioned before, elastomers may be deposited on a solid surface without use of a solvent or other liquid employed to improve its tractability, e.g., in hot-melt applications at an elevated temperature sufficient for at least partial melting of the elastomer. However, for many end uses, the elastomers are applied in emulsions, suspensions, or solutions using an appropriate liquid vehicle, e.g., water or an organic substance or mixture thereof. In solvent-based systems, the organic vehicle may be any of a great variety of the known organic solvents, but is commonly predominantly or even essentially completely composed of at least one normally liquid hydrocarbon, e.g., an aliphatic hydrocarbon such as n-heptane, n-hexane or cyclohexane and/or an aromatic hydrocarbon such as toluene, xylene or benzene. Studies of the multi-ring compounds used in this invention have shown them to be very compatible (e.g., miscible in twice their weight of solvent) in such diverse organic solvents as toluene, xylene, benzene, hexanes, n-heptane, cyclohexane, paraffin oils, caster oil, naphthenic oil, isobutanol, acetone, butyl acetate, methyl ethyl ketone, methyl isobutyl ketone and carbon tetrachloride.

Especially in large scale industrial uses, it is highly desirable to further limit the amount of hydrocarbon which must be removed from compositions used in depositing the elastomer and which therefore require effluent disposal measures to prevent environmental and/or health hazards. It is an important aspect of this invention that use of the aforedescribed compounds substantially decreases the amount of vehicle needed for such elastomer applications and, in some cases, largely or completely eliminates the need to use certain undesirable vehicles, e.g., aromatic compounds such as toluene, xylene and the like. Hence in embodiments of this invention utilizing an organic solvent in an amount sufficient to substantially completely dissolve the elastomer, it is a significant aspect of the invention that such an amount of the solvent can be less than that required to substantially completely dissolve the elastomer in the absence of the elastomer modifier. Another important advantage of the invention is that, as a consequence of improved elastomer tractability, it permits the substitution of lower-cost elastomers of less inherent tractability for those of higher cost and greater inherent tractability, e.g., substitution of SBS or even SBR for natural rubber or SIS.

The following Examples are to illustrate specific embodiments of the invention and do not imply any limitation on the scope of the invention. In these Examples, all benzylation reactions were carried out under a nitrogen atmosphere. MW's and average AHP's by weight (shown in Table I for the final products prepared in Examples 5-36) were determined by gel permeation chromatography (GPC) and proton nuclear magnetic resonance (NMR), respectively. The GPC determinations were carried out using a Waters Associates (Milford, Mass.) M-600 pump, an Altex Scientific, Inc. (Berkeley, Calif.) 210 injector, a series of two DuPont stainless steel 6.2 mm I.D.×25 cm long Zorbax columns (PSM-60S and —1000S) packed with porous silica microspheres, a Waters Associates Differential Refractomer Model 401, and a Tektronix (Beaverton, Org.) Calculator Model 31, Digital Multimeter DM501 and Digital Plotter Model 4661. The determinations were made in relation to a log MW x elution time linear calibration curve developed with 6 separate polystyrene standards having peak MW's of 4,000, 9,000, 17,500, 50,000, 110,000 and 390,000, and were carried out at 25° C. and about 500 psig column pressure using a flow rate of 0.5 ml/minute of a 1% solution in non-spectro grade tetrahydrofuran. Detector attenuation was 16X, and each sample and standard (100 microliters) was pre-filtered using a 0.45 micron filter. All MW's herein are expressed with reference to determinations carried out as just described or by an equivalent method.

EXAMPLE 1

This Example illustrates use of this invention for improvements in tractability of a commercially available styrene/isoprene/styrene block copolymer having the following characteristics: Styrene/Rubber Ratio—14/86; Shore A Hardness—37; Specific Gravity—0.92; 300% Modulus—7.03 kg/cm$^2$ (ASTM D412, jaw speed 25.4 cm./min.); and Melt Viscosity, Condition G—9 gms./10 min.

This Example was carried out using a mixture of polyphenyls conventionally hydrogenated (Raney Nickel; 205°; 1,000 psig H$_2$) to the extent that 40% of the rings in such polyphenyls were saturated, leaving the remaining 60% of such rings aromatic (AHP=40). The mixture contained 46% m-terphenyl, 24% p-terphenyl, 7% o-terphenyl, 22% of the various quaterphenyl isomers and 1% higher-MW polyphenyls (mostly pentaphenyls). The hydrogenated mixture was a clear, oily liquid having a T$_g$ range from "53° to −48° (ASTM D3418-75) and MW's which were 72% between 200 and 500 and 95% between 120 and 550 (calculated average 262). The average MW's were 265 by wt. and 231 by number. This mixture was compared with a plasticizer (butyl benzylphthalate), a normally liquid tackifier (synthetic polyterpene resin) and an extender oil (400 MW—50% naphthenic, 49% paraffinic and 1% aromatic) commonly used in elastomer adhesive compositions. Each combination was thoroughly mixed at room temperature and, at four different ratios of each polyphenyl to the elastomer, the maximum percent solids pourable at room temperature in heptane (no aromatic solvent) was determined on the basis of visual movement within 10 seconds from a 300 ml. beaker of the composition suddenly inverted. Results were as follows:

| Polyphenyl/Elastomer Ratio | Maximum % Solids In Pourable Composition | | | |
|---|---|---|---|---|
| | 80/20 | 70/30 | 60/40 | 50/50 |
| Modifier | | | | |
| Hydrogenated polyphenyls (this invention) | 90 | 78 | 64 | 50 |
| Butyl benzyl phthalate | Precipitate | 45 | 40 | 39 |
| Extender Oil | 53 | 42 | 40 | 41 |
| Synthetic polyterpene resin | 50 | 41 | 35 | rubbery |

EXAMPLE 2

This Example repeated the comparisons in Example 1 except that the elastomer was a styrene/butadiene/styrene block copolymer having the following characteristics: Styrene/Rubber Ratio—30/70; Shore A Hardness—71; Specific Gravity—0.94; 300% Modulus—28.12 kg/cm$^2$ (ASTM D412, jaw speed 25.4 cm./min.); and Melt Viscosity, Condition G - <1 gm./10 min.

| Polyphenyl/Elastomer Ratio | Maximum % Solids In Pourable Composition | | | |
|---|---|---|---|---|
| | 80/20 | 70/30 | 60/40 | 50/50 |
| Modifier | | | | |
| Hydrogenated polyphenyls | 90 | 75 | 63 | 50 |
| Butyl benzyl | 60 | 40 | 22 | paste |
| Extender Oil | ← | rubbery | | → |
| Synthetic polyterpene resin | 45 | ← | rubbery | → |

EXAMPLE 3

This Example illustrates that, despite the tractability improvements of the kind shown in Examples 1-2, the hydrogenated polyphenyls used in those Examples do not significantly decrease strength of the elastomer.

In this Example, the hydrogenated polyphenyl mixture used in Examples 1-2 was compared with the tackifier used in those Examples. In Run A, 25 parts of the elastomer used in Example 1 were thoroughly hand-mixed with 50 parts of toluene and 25 parts of the tackifier. In Run B, 9 parts of the hydrogenated polyphenyls mixture were substituted for 9 of the 25 parts of tackifier used in Run A. These mixtures were then subjected to the shear adhesion (holding power) test designated PSTC-7 in TEST METHODS FOR PRESSURE SENSITIVE TAPES, 7th Edition, Pressure Sensitive Tape Council, Glenview, Ill. (1976). This test (at 60°) measures the slippage of a 2.54-cm. wide polyester tape covered with a 0.025 mm. thickness of the test mixture and then rolled against a near-vertical flat steel surface. In this Example it was found that after 78 hours, the Run A tape had slipped 12 mm., and the Run B tape had not undergone any measurable slip.

EXAMPLE 4

This Example illustrates the unexpected effect of the polyphenyls used in Examples 1-3 on $T_g$ of the major phases of various elastomers, when they are thoroughly mixed at one part polyphenyl per two parts elastomer. The polyphenyl mixture used was that employed in Example 1 ($T_g$ range of $-48°$ to $-53°$ by ASTM method D3418-75). The measurements in this Example, by Rheovibron Model RHEO-320 (Imass Corp., Accord, Mass.), had the results shown below when Elastomer A was natural rubber, Elastomer B was that used in Example 1, Elastomer C was that used in Example 2, and Elastomer D was a nonstereospecific high bound styrene (23.5% block polystyrene) SBR. In each of Elastomers B-D, the polystyrene phase $T_g$ (120° C.) was unchanged by inclusion of the polyphenyls. The lowest $T_g$'s of the four elastomers (those of the continuous, rubber phase of each) were changed as follows:

| Elastomer | $T_g$ Without Modifier | $T_g$ With Modifier |
|---|---|---|
| A | $-60°$ | $-51°$ |
| B | $-55°$ | $-47°$ |
| C | $-80°$ | $-75°$ |
| D | $-46°$ | $-45°$ |

EXAMPLE 5

A mixture of polycyclohexylated polyphenyls was prepared by heating a mixture of 39 g. biphenyl, 122 g. terphenyls and 52 g. quaterphenyls to 50° in 161 g. cyclohexane, saturating the mixture with anhydrous HCl, adding 4.5 g. AlCl₃ and the 340 g. cyclohexene over 3 hours while holding the temperature at 65°-70°, separating the AlCl₃ by precipitation with Ca(OH)₂ and filtration, and then removing the cyclohexane by vacuum/steam distillation. Yield was 531 g. (94% of theoretical) of a hard, brittle solid having a melting range of 88°-105° and MW's which were 93% between 200 and 1300 (calc. avg. 505).

EXAMPLE 6

A mixture of polycyclohexylated polyphenyls was prepared essentially as in Example 5 except that the biphenyl was omitted. Yield was 91.5% of theoretical of a hard, brittle solid having a melting range of 81°-98° and MW's which were 94% between 200 and 1300 (calc. avg. 575).

EXAMPLE 7

A mixture of hydrogenated polybenzylated polyphenyls was prepared by adding 1,084 g. benzyl chloride dropwise over 2 hours to a 100° mixture of 200 g. pentaphenyls, 6 g. nitromethane (to minimize tars formation) and 5.4 g. AlCl₃, holding the mixture at 100° for an additional 3 hours, separating the catalyst by Ca(OH)₂/CaO precipitation and filtration, separating unreacted biphenyl and other organic low-boiling materials by vacuum/steam distillation, dehydrating the residue for 30 minutes at 125° and 50 mm., hydrogenating the resulting yield of 1,526 g. (97.5% of theoretical) with 1,000 psig hydrogen and 50 g. Raney Nickel at 205° until hydrogenation proceeded to the desired level, maintaining the mixture at 205° until pressure fell below 100 psig, cooling below 80° C., and removing the catalyst by filtration leaving a clear, light yellow, very viscous gel having MW's which were 57% between 400 and 1500, 74% between 300 and 2000, and 90% between 200 and 2500 (calc. avg. 441).

EXAMPLE 8

A mixture of hydrogenated polybenzylated polyphenyls was prepared essentially as in Example 7 except that the amounts of terphenyls and quaterphenyls were 280 g. and 120 g., respectively (the intermediate yield of 1,336 g. was 97.4% of theoretical) and hydrogenation was continued until the AHP in this product (a clear, light orange, very viscous gel) was 60.7. The product MW's were 76% between 400 and 2000, 88% between 300 and 3000, and 97% between 200 and 3300 (calc. avg. 484).

EXAMPLE 9

Example 8 was essentially duplicated except that hydrogenation was continued until the AHP was 47.4 (calc. avg. MW 488).

EXAMPLE 10

A mixture of hydrogenated polybenzylated biphenyls was prepared under reaction conditions essentially as in Example 7 except that the amount of added benzyl chloride was 6.0 moles per mole of biphenyl, the mixture was held at 120° for a total of 1.5 hours after benzyl chloride addition at 75°-78°, and hydrogenation of the separated benzylation product was continued until the AHP was 25.9. This product was a clear, light yellow, glassy solid having MW's which were 65% between 400 and 2000, 80% between 300 and 2500, and 92% between 200 and 3000 (calc. avg. 722).

EXAMPLE 11

Example 10 was essentially duplicated except that the benzylation reaction was carried out at 72°-75° for a total of 7.5 hours (the yield of 634 g. was 91.2% of theoretical) and hydrogenation was continued until the AHP was 45.9. This product was a semi-clear, light orange semi-solid having MW's which were 80% between 400 and 8000, 87% between 300 and 9000, and 95% between 200 and 10,000 (calc. avg. 710).

EXAMPLE 12

Example 10 was essentially duplicated except that the amount of benzyl chloride was 0.75 mole per mole of biphenyl, the benzylation reaction was carried out at 74° for 1.9 hours and then 110° for an additional 4.1 hours (the yield of 1,254 g. was 98.4% of theoretical) and hydrogenation was continued until the AHP was 59.4. This product was a clear, light yellow, viscous oil having MW's which were 55% between 400 and 1000, 76% between 300 and 1500, and 92% between 200 and 2000 (calc. avg. 430).

EXAMPLE 13

A mixture of hydrogenated polybenzylated polyphenyls was prepared by adding 1,044 g. benzyl chloride dropwise over 2 hours to a 145° mixture of 400 g. terphenyls, 171 g. quaterphenyls, 6 g. pentaphenyls, 7 g. nitromethane, and 5.3 g. AlCl$_3$, holding the mixture at 145° for an additional 1.5 hours, and then separating product essentially as in Example 7, yielding 1,302 g. (98.6% of theoretical) of a clear, glassy solid which was then hydrogenated as in Example 7 until the AHP in the product (a clear, dark brown, glassy solid) was 47.2. The product MW's were 50% between 400 and 1000, 76% between 300 and 1500, and 92% between 200 and 2000 (calc. avg. 586).

EXAMPLE 14

Example 13 was essentially duplicated except that 1,139 g. benzyl chloride was added to 321 g. terphenyls, 137 g. quaterphenyls and 5 g. pentaphenyls over 6.25 hours, producing 1,258 g. (98.7% of theoretical) of a hard, clear, glassy solid having mean MW's of 450 (wt.) and 332 (number), and hydrogenation was continued until the AHP in the product (a light orange, glassy solid) was 33.3. MW's of this product were 43% between 400 and 1000, 68% between 300 and 1500, and 87% between 200 and 2000 (calc. avg. 676).

EXAMPLE 15

Example 14 was essentially duplicated except that hydrogenation was terminated when the AHP was 49.6. This product was a clear, dark brown, glassy solid (calc. avg. MW 704).

EXAMPLE 16

Example 14 was essentially duplicated except that the benzyl chloride was added over 1.2 hours, the reaction temperature was maintained at 158° for a total of 3.2 hours yielding 1,256 g. (98.6% of theoretical) of a very hard, glassy solid, and hydrogenation was terminated when the AHP was 58.2. This product was an opaque, dark brown, glassy solid having MW's which were 78% between 400 and 2000, 89% between 300 and 3000, and 97% between 200 and 4000 (calc. avg. 700).

EXAMPLE 17

A mixture of hydrogenated polybenzylated polyphenyls was prepared by adding 506 g. benzyl chloride dropwise over 2.25 hours to a 120°-140° mixture of 108 g. terphenyls, 46 g. quaterphenyls, 4 g. nitromethane and 2.6 g. AlCl$_3$, maintaining the mixture at 180° for an additional 3 hours, and then recovering 503 g. (97.6% of theoretical) of an amber, medium-hard, glassy solid as in Example 7. This benzylation product was hydrogenated as in Example 7 until the AHP in the final product was 44.5, providing a clear, light orange solid having MW's which were 83% between 400 and 3000, 91% between 300 and 4000, and 97% between 200 and 5000 (calc. avg. 711).

EXAMPLE 18

A mixture of hydrogenated polybenzylated toluenes was prepared by adding 633 g. benzyl chloride dropwise over 1 hour to a 48° mixture of 92 g. toluene, 100 g. cyclohexane, 3.7 g. AlCl$_3$ and 5.4 g. nitromethane, maintaining the mixture at 48°-65° for an additional 4 hours, and then separating catalyst and recovering the benzylation product as in Example 7. This yielded 523 g. (96.3% of theoretical) of a glassy solid which softened at 24°. Hydrogenation was then carried out until the AHP in the final product (a clear, light yellow solid) was 31.8. MW's of this product were 75% between 400 and 1500, 88% between 300 and 2000, and 98% between 200 and 2500 (calc. avg. 561).

EXAMPLE 19

A mixture of hydrogenated polybenzylated toluenes was prepared essentially as in Example 18 except that the molar ratio of benzyl chloride to toluene was 6, reaction temperature was allowed to reach 125°, and the reaction was terminated after 2 hours. This very dark benzylation product was hydrogenated as in Example 7 until the AHP in the final product (a clear, light yellow, glassy solid) was 27.4. This product had MW's which were 78% between 400 and 2500, 89% between 300 and 3000, and 92% between 200 and 4000 (calc. avg. 658).

EXAMPLE 20

A mixture of hydrogenated polybenzylated toluenes was prepared essentially as in Example 18 except that the cyclohexane was omitted, the quantities of the other mixture constituents were benzyl chloride 1,899 g., toluene 138 g., AlCl$_3$ 12 g., and nitromethane 17 g., and addition of the benzyl chloride took place over 3 hours. This yielded 1,470 g. (98.6% of theoretical) of a hard, brittle solid melting between 37° and 50°. Hydrogenation of this product was continued until the AHP was 55.8%, providing a clear, light yellow, glassy solid having MW's which were 87% between 400 and 2500, and 94% between 300 and 3500 (calc. avg. 1006).

EXAMPLE 21

A mixture of hydrogenated polybenzylated toluenes was prepared essentially as in Example 20 except that the reaction temperature was allowed to rise to 60° and the hydrogenation was continued until the AHP was 44.8%. This produced a clear, light yellow, glassy solid having MW's which were 89% between 400 and 3000, and 96% between 300 and 4000 (calc. avg. 1011).

EXAMPLE 22

A mixture of polybenzylated toluenes was prepared essentially as in Example 19 except that the molar ratio of benzyl chloride to toluene was 10, the benzylation reaction was continued for 14 hours, and hydrogenation was continued until the AHP was 33.3%, providing a clear, light yellow, glassy solid having MW's which were 91% between 400 and 5000, and 96% between 300 and 6000 (calc. avg. 1015).

EXAMPLE 23

A mixture of hydrogenated polybenzylated toluenes was prepared essentially as in Example 20 except that hydrogenation was continued until the AHP was 24.6%, providing a clear, light yellow glassy solid (calc. avg. MW 1030).

EXAMPLE 24

A mixture of hydrogenated polybenzylated toluenes was prepared essentially as in Example 22 except that the molar ratio of benzyl chloride to toluene was 14, the reaction temperature was permitted to rise to 140°, the reaction was terminated after 1.7 hours, and the hydrogenation was carried out until the AHP was 31.4%, providing a clear, light orange, glassy solid having MW's which were 90% between 400 and 6000, and 95% between 300 and 8000 (calc. avg. 1399).

EXAMPLE 25

A mixture of hydrogenated polybenzylated xylenes was prepared essentially as in Example 22 except that xylene was substituted for toluene on an equimolar basis, the reaction was terminated after 30 minutes, and hydrogenation was continued until the AHP was 43.3%, providing an opaque, light yellow, powdery solid having MW's which were 88% between 400 and 4000, and 95% between 300 and 7000 (calc. avg. 1032).

EXAMPLE 26

A mixture of polybenzylated biphenyls was prepared essentially as in Example 12 except that the reaction temperature was permitted to rise to 82° and held there for a total of 4.3 hours. To an 80° mixture of 466 g. of that reaction product and 7 g. $AlCl_3$, 691 g. cyclohexene was added dropwise over 3.6 hours while permitting the mixture temperature to rise to 105°, and then to 115° for an additional 3.2 hours. Product separation as in Example 7 yielded 1,097 g. (94.8% of theoretical) of a hard, glassy solid melting between 45°–50° and having MW's which were 69% between 400 and 3000, 81% between 300 and 4000, and 92% between 200 and 5000 (calc. avg. 754).

EXAMPLE 27

A mixture of polycyclohexylated polybenzylated diphenylmethanes was prepared by adding 127 g. benzyl chloride and 192 g. cyclohexene over 1.8 hours to a 24° mixture of 56 g. diphenylmethane and 2.4 g. $AlCl_3$ while permitting the mixture temperature to rise to 60° and then to 105° during an additional 5.3 hours. Product separation as in Example 5 yielded 271 g. (80.4% of theoretical) of a soft, glassy solid having the MW's which were 58% between 400 and 3000, 75% between 300 and 4000, and 90% between 200 and 5000 (calc. avg. 445).

EXAMPLE 28

A mixture of polycyclohexylated polybenzylated toluenes was prepared by adding 184 g. cyclohexene dropwise over 2.1 hours to a 53° mixture of 150 g. cyclohexane, 3 g. $AlCl_3$ and 184 g. of a mixture of polybenzylated toluenes prepared as in Example 18. After holding the mixture at 65° for an additional 2.5 hours, product separation as in Example 5 yielded 230 g. (62.4% of theoretical) of a soft, glassy solid having MW's which were 73% between 400 and 2000, 86% between 300 and 3000, and 96% between 200 and 3500 (calc. avg. 1083).

EXAMPLE 29

A mixture of polybenzylated toluenes was prepared as in Example 20. Without further hydrogenation, the AHP in this hard, brittle product was 82 (calc. avg. MW 992).

EXAMPLE 30

A mixture of polyalkylated polybenzylated toluenes was prepared by adding 380 g. benzyl chloride dropwise over 4 hours to a stirred 5° mixture of 92 g. toluene, 100 g. cyclohexane, 7 g. $AlCl_3$ and 6 g. nitromethane, after which the mixture was held at 2° for an additional hour and then warmed to 24° for an additional 16 hours. 333 g. of a mixture composed of 19% hexenes, 55% octenes and 26% decenes was then added dropwise over 4 hours while stirring at 24°–35°. Maintaining the mixture at 24°–33° for an additional 19 hours and then separating product as in Example 5 yielded 628 g. (90% of theoretical) of a liquid having MW's which were 55% between 400 and 2000, 73% between 300 and 4000, and 90% between 200 and 6000 (calc. avg. 695).

EXAMPLE 31

A mixture of polyoctylated polyphenyls was prepared by adding 561 g. of a mixture of 1- and 2-octenes dropwise over 2.5 hours to a 40°–55° mixture of 162 g. terphenyls, 69 g. quaterphenyls, 200 g. cyclohexane and 5 g. $AlCl_3$. Holding the mixture at 55° for an additional 5.5 hours and then separating product as in Example 5 yielded 773 g. (97% of theoretical) of a liquid having MW's which were 70% between 400 and 2000, 86% between 300 and 3000, and 95% between 200 and 3500 (calc. avg. 766).

EXAMPLE 32

A mixture of polyalkylated polybenzylated toluenes was prepared by adding 190 g. benzyl chloride dropwise over 1.4 hours to a 25°–34° mixture of 46 g. toluene, 4 g. $AlCl_3$ and 4 g. nitromethane, holding the mixture at 50° C. for an additional 3.9 hours, then adding dropwise 272 g. of a mixture composed of 19% hexenes, 55% octenes and 26% decenes over 1.4 hours and holding the resulting mixture of 70°–90° for an additional 3 hours. Product separation as in Example 5 yielded 424 g. (93.6% of theoretical) of a liquid having MW's which were 71% between 400 and 2000, 84% between 300 and 3000, and 95% between 200 and 3500 (calc. avg. 918).

EXAMPLE 33

A mixture of polyalkylated polyphenyls was prepared by adding dropwise 277 g. of a mixture composed of 19% hexenes, 55% octenes and 26% decenes over 2.3 hours to a 24°–33° mixture of 81 g. terphenyls, 35 g. quaterphenyls, 200 g. cyclohexane and 2.6 g. $AlCl_3$, and then holding the mixture at 34°–40° for an additional 3.7 hours. Product separation as in Example 5 yielded 367 g. (93% of theoretical) of a slurry having MW's which were 70% between 400 and 1500, 86% between 300 and 2000, and 96% between 200 and 2500 (calc. avg. 486).

EXAMPLE 34

A mixture of of polyhexadecylated polybenzenes was prepared by simultaneously adding benzyl chloride and hexadecene to a mixture to cyclohexane and $AlCl_3$, and then holding the mixture at 135° for 18 hours. MW's of this product were 92% between 400 and 40,000 and 96% between 300 and 50,000.

EXAMPLE 35

A mixture of hexadecylated polybenzylated toluenes (benzyl:toluene mole ratio of 10:1) was prepared by adding benzyl chloride and hexadecene to 20°–24° toluene containing $AlCl_3$ and then holding the mixture at 150° C. for 1 hour. Separation of the very dark product (yield 99% of theoretical) provided a liquid having MW's which were 85% between 400 and 10,000 and 95% between 300 and 20,000 (calc. avg. approx. 3200).

EXAMPLE 36

A mixture of polyhexadecylated polybenzylated toluenes (benzyl:toluene mole ratio of 4:1) was prepared by simultaneously adding benzyl chloride and hexadecene dropwise to 80° toluene containing $AlCl_3$ over 1 hour. The very dark product had MW's which were 87% between 400 and 10,000 and 95% between 300 and 20,000 (calc. avg. approx. 1370).

The compounds prepared in the preceding Examples 5–36 were blended with an elastomer conventionally used in hot-melt adhesives and compared with commercially available tackifiers for their effects on adhesive strength of the resulting elastomer compositions. These tests were carried out with elastomer compositions composed of equal weights of DuPont's ELVAX® 250 copolymer (72% ethylene and 28% vinyl acetate) having a melt index of 25 g/10 minutes by ASTM D1238, paraffin wax having a melting point of 62° (Sun Petroleum Products Co.) and the indicated compounds being evaluated. Composition strengths were measured by ASTM D1876-72, the "T-Peel" test which measures the force required to separate in opposite directions at 12.7 cm./min. (jaw speed 25.4 cm./min.), two 2.54-cm, wide strips of the indicated materials which have been bonded with 0.127 mm. of the elastomer composition under momentary light pressure in a Nordberg Press at 175°. The three materials employed were 5.9 mm. thick high density polyethylene, 1.9 mm. thick Mylar® polyethylene terephthalate (DuPont) and 1.9 mm. thick industrial grade, smooth-finish aluminum foil. Averaged results are shown in Table I in kilograms of separation force required per meter of width of the adhered materials.

TABLE I

| | AVG. MW'S | | AROMATIC | T-PEEL RESULTS, KG/M | | |
|---|---|---|---|---|---|---|
| EXAMPLE | BY WT. | BY NO. | HYDROGEN PERCENTAGE | POLYETHYLENE | POLYETHYLENE TEREPHTHALATE | ALUMINUM |
| POLYCYCLOALKYLATED POLYPHENYLS (NO ALIPHATIC LINKAGES) | | | | | | |
| 5 | 461 | 378 | 38.0 | 49 | 56 | 30 |
| 6 | 475 | 394 | 38.1 | 89 | 49 | — |
| HYDROGENATED POLYBENZYLATED POLYPHENYLS | | | | | | |
| 7 | 534 | 378 | 38.5 | 222 | 11 | 25 |
| 8 | 766 | 529 | 60.7 | 174 | 15 | — |
| 9 | 772 | 533 | 47.4 | 228 | 9 | — |
| 10 | 632 | 428 | 25.9 | 190 | 85 | — |
| 11 | 1764 | 672 | 45.9 | 54 | 5 | 37 |
| 12 | 540 | 396 | 59.4 | 86 | 3 | 25 |
| 13 | 510 | 389 | 47.2 | 177 | 49 | 25 |
| 14 | 450 | 332 | 33.3 | 176 | 115 | 29 |
| 15 | 469 | 346 | 49.6 | — | 9 | 36 |
| 16 | 780 | 549 | 58.2 | — | 13 | 32 |
| 17 | 953 | 619 | 44.5 | 56 | 1 | 26 |
| HYDROGENATED POLYBENZYLATED TOLUENES | | | | | | |
| 18 | 692 | 523 | 31.8 | 222 | 125 | 29 |
| 19 | 888 | 584 | 23.8 | 140 | 32 | — |
| 20 | 1056 | 730 | 55.8 | 94 | 3 | 30 |
| 21 | 1316 | 888 | 44.8 | — | 9 | 20 |
| 22 | 1604 | 898 | 33.3 | 13 | 3 | 53 |
| 23 | 1050 | 695 | 24.6 | 11 | 4 | 26 |
| 24 | 2225 | 1118 | 31.4 | 13 | 1 | 60 |
| 25 | 1285 | 780 | 43.3 | — | 1 | 51 |
| POLYCYCLOALKYLATED AROMATICS (CONTAINING ALIPHATIC LINKAGES) | | | | | | |
| 26 | 833 | 474 | 38.3 | 80 | 29 | 29 |
| 27 | 977 | 449 | — | 70 | 5 | — |
| 28 | 747 | 508 | 68.0 | 42 | 1 | 48 |
| POLYBENZYLATED TOLUENES | | | | | | |
| 29 | 1041 | 720 | 82 | 152 | 6 | 93 |
| AROMATICS ALKYLATED WITH NON-CYCLIC OLEFINS | | | | | | |
| 30 | 598 | 379 | 50 | 55 | 1 | 19 |
| 31 | 654 | 471 | 30 | 35 | 31 | — |
| 32 | 703 | 479 | 33.6 | 39 | 1 | — |
| 33 | 622 | 478 | 29.5 | 6 | 19 | — |
| 34 | 12,343 | 2117 | 30 | 6 | 10 | — |
| 35 | 2794 | 950 | 30 | 2 | 6 | — |
| 36 | 3681 | 1165 | 30 | — | 5 | — |

We claim:

1. A composition comprising a normally solid, essentially organic elastomer and at least one compound consisting of at least 5 hydrocarbon rings including at least one aromatic ring and at least one saturated ring free to rotate independently of at least one aromatic ring in the molecule of said compounds, at least one divalent aliphatic radical linking two of said rings, and from zero to about two alkyl substituents on said rings, said compound having a molecular weight between about 400 and about 8,000.

2. A composition of claim 1 containing said at least one compound in an amount greater than 15% up to about 100% by weight of said elastomer.

3. A composition of claim 2, said at least one aromatic ring containing from about 25% to about 70% of the hydrogen in said compound.

4. A composition of claim 2 wherein said at least one compound is a mixture having an average molecular weight (by weight) between about 400 and about 2500.

5. A composition of claim 2 wherein said elastomer is at least about 15% composed of polymeric domains which are normally substantially soluble in toluene and not substantially soluble in n-hexane.

6. A composition of claim 2 wherein said elastomer is selected from the group consisting of natural rubber, copolymers of styrene and at least one diene containing from 4 to about 5 carbon atoms, and mixtures thereof.

7. A composition of claim 2 wherein said elastomer is selected from the group consisting of ethylene/vinyl acetate copolymers containing at least about 10% vinyl acetate by weight of ethylene.

8. A composition containing a normally solid, essentially organic elastomer and at least one compound consisting of at least 5 aromatic hydrocarbon rings, a plurality of divalent aliphatic radicals each linking two of said rings, and from zero to about two alkyl substituents on said rings, said compound having a molecular weight between about 400 and about 8000, and said plurality being at least about half the number of rings in said compound.

9. A composition of claim 8 containing said at least one compound in an amount greater than 15% up to about 100% by weight of said elastomer.

10. A composition of claim 9 wherein said elastomer is an ethylene/vinyl acetate copolymer containing at least about 10% vinyl acetate by weight of ethylene.

11. A composition of claim 9 wherein said at least one compound is a mixture having an average molecular weight (by weight) between about 400 and about 2500, said aliphatic radical is methylene, and said alkyl is methyl.

12. A composition containing a normally solid, essentially organic elastomer selected from natural rubber, polymers of at least one diene containing from 4 to about 5 carbon atoms, copolymers of said at least one diene with at least one vinyl aromatic compound, polyacrylates, polyamides, polyvinyl acetate, silicone rubbers, urethane rubbers, ethylene/vinyl acetate copolymers containing at least about 15% vinyl acetate by weight, and mixtures thereof, and at least one compound consisting of at least 3 hydrocarbon rings including at least one aromatic ring and at least one saturated ring free to rotate independently of at least one aromatic ring in the molecule of said compound, said compound having a molecular weight between about 200 and about 2000.

13. A composition of claim 12, said compound having the structural formula

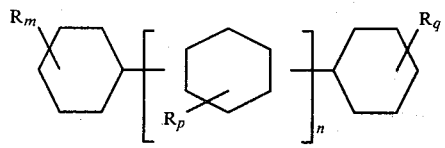

wherein each R is independently phenyl or cycloalkyl, n is zero or an integer from one to about three, m and q are each independently zero or an integer from one to five, p is zero or an integer from one to four, and the sum of m, n, p and q is from one to about thirteen.

14. A composition of claim 13 comprising an amount of said at least one compound sufficient to raise the lowest glass transition temperature of said elastomer.

15. A composition of claim 13 containing said at least one compound in an amount greater than 15% up to about 100% by weight of said elastomer.

16. A composition of claim 13 further comprising a hydrocarbon solvent in an amount in which said elastomer is soluble in the presence of said at least one compound but not soluble in the absence thereof.

17. A composition of claim 13 wherein said elastomer is selected from the group consisting of natural rubber, polymers of at least one diene containing from 4 to about 5 carbon atoms, copolymers of styrene and said at least one diene, and mixtures thereof, said at least one aromatic ring containing from about 20% to about 80% of the hydrogen in said compound.

18. A composition of claim 17 wherein the sum of m, n, p and q is from 3 to about 10, said at least one aromatic ring containing from about 25% to about 70% of the hydrogen in said compound.

19. A composition of claim 13 wherein the elastomer is selected from said ethylene/vinyl acetate copolymers, and said compound is a product of hydrogenating a more highly aromatic compound having the same carbon skeleton.

20. A composition of claim 19 wherein the sum of m, n, p and q is from 3 to about 10, said at least one aromatic ring containing from about 25% to about 70% of the hydrogen in said compound.

21. A composition of claim 13 wherein said at least one compound is a mixture having an average molecular weight (by weight) between about 200 and about 1500.

* * * * *

UNITED STATES PATENT AND TRADEMARK OFFICE
CERTIFICATE OF CORRECTION

PATENT NO. : 4,404,311
DATED : Sept. 13, 1983
INVENTOR(S) : Thomas C. Mathis, et al It is certified that error appears in the above-identified patent and that said Letters Patent are hereby corrected as shown below:

Column 2, line 32, "as" should be corrected to read --an--.

Column 5, line 29, "quarterphenyl" should read --quaterphenyl--.

Column 9, line 48, "Org." should read --Oreg.--.

Column 10, line 60, in the "Modifier" list, "Butyl benzyl" should read --Butyl benzyl phthalate--.

Column 12, line 7, after "200 g.", add --biphenyl, 410 g. terphenyls, 176 g. quaterphenyls, 6 g.--.

Signed and Sealed this

Twentieth Day of March 1984

[SEAL]

Attest:

GERALD J. MOSSINGHOFF

Attesting Officer

Commissioner of Patents and Trademarks